United States Patent
Samadi et al.

(10) Patent No.: US 8,999,994 B2
(45) Date of Patent: Apr. 7, 2015

(54) DERIVATIVES OF PROPARGYLAMINE HAVING NEUROPROTECTIVE CAPACITY FOR THE TREATMENT OF ALZHEIMER'S AND PARKINSON'S DISEASES

(75) Inventors: Abdelouahid Samadi, Madrid (ES); José Luis Marco Contelles, Madrid (ES); Irene Bolea Tomás, Barcelona (ES); Francisco Javier Luque Garriga, Barcelona (ES); Mercedes Unzeta López, Barcelona (ES)

(73) Assignees: Consejo Superior de Investigaciones Cientificas, Madrid (ES); Universitat Autonoma de Barcelona, Barcelona (ES); Universidad de Barcelona, Barcelona (ES)

( * ) Notice: Subject to any disclaimer, the term of this patent is extended or adjusted under 35 U.S.C. 154(b) by 0 days.

(21) Appl. No.: 13/635,894

(22) PCT Filed: Mar. 18, 2011

(86) PCT No.: PCT/ES2011/070186
§ 371 (c)(1), (2), (4) Date: Sep. 18, 2012

(87) PCT Pub. No.: WO2011/113988
PCT Pub. Date: Sep. 22, 2011

(65) Prior Publication Data
US 2013/0012522 A1    Jan. 10, 2013

(30) Foreign Application Priority Data
Mar. 18, 2010    (ES) .................................. 201030404

(51) Int. Cl.
| C07D 401/12 | (2006.01) |
| C07D 403/12 | (2006.01) |
| A61K 31/496 | (2006.01) |
| A61K 31/445 | (2006.01) |
| A61P 25/28 | (2006.01) |

(52) U.S. Cl.
CPC ............ *C07D 401/12* (2013.01); *C07D 403/12* (2013.01)

(58) Field of Classification Search
CPC .. C07D 401/12; C07D 403/12; A61K 31/496; A61K 31/445; A61K 31/404
USPC .............. 514/323, 254.09; 548/504; 546/201; 544/373
See application file for complete search history.

(56) References Cited

FOREIGN PATENT DOCUMENTS

CA    2187460    *    8/1996    ............. A61K 31/40

* cited by examiner

*Primary Examiner* — Sreeni Padmanabhan
*Assistant Examiner* — Irina Neagu
(74) *Attorney, Agent, or Firm* — Linda B. Huber; Nixon Peabody LLP

(57) ABSTRACT

The present invention relates to a compound of formula (I):

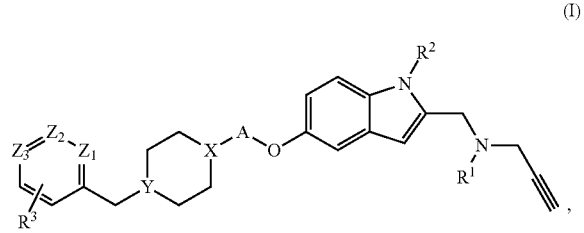

wherein: $R^1$ and $R^2$ are selected from among H and C1-C10 alkyl; $R^3$ is selected from among H, $-OR^4$, N, $-CN$, $-C(O)R^4$, $-C(O)OR^4$, $-C(O)NR^4R^5$, $-C=NR^4$, $-OC(O)R^4$, $-NR^4R^5$, $-NR^4C(O)R^5$, $-NO_2$, $-N=CR^4R^5$, halogen and C1-C10 alkyl, wherein $R^4$ and $R^5$ are selected from among H, alkyl, alkenyl, cycloalkyl and aryl; X, Y, $Z^1$, $Z^2$ and $Z^3$ are selected independently from among CH and N; A is selected from among $(CH_2)_n$, NH, O and CO, wherein n is an integer between 1 and 6, to the procedure for the obtainment of said compounds, to a pharmaceutical composition comprising said compound, and to the use thereof in the treatment of a neurodegenerative disease, more particularly treatment of Alzheimer's or Parkinson's disease.

13 Claims, No Drawings

DERIVATIVES OF PROPARGYLAMINE HAVING NEUROPROTECTIVE CAPACITY FOR THE TREATMENT OF ALZHEIMER'S AND PARKINSON'S DISEASES

CROSS-REFERENCE TO RELATED APPLICATIONS

The present application is the National Phase of International Application PCT/ES2011/070186, filed Mar. 18, 2011, which designated the United States. This application also includes a claim of priority under 35 U.S.C. §119(a) and §365(b) to Spanish patent application No. P201030404, filed Mar. 18, 2010.

This invention concerns a series derived from N-methyl-N-{[(1-methyl-5-alkoxy)-1H-indol-2-yl]methyl}prop-2-yn-1-amine, that are multipotent inhibitors of monoamine oxidase A and B enzymes, acetylcholinesterase and butyrylcholinesterase, with possible application within the pharmaceutical industry field as medications to cure, delay, or alleviate neurodegenerative diseases such as Alzheimer's disease and Parkinson's disease.

PRIOR ART

Alzheimer's disease (AD), the most common dementia in older people, is a complex neurodegenerative disorder of the central nervous system, characterized by a progressive loss of intellectual abilities (memory, language, and reasoning) and psychiatric disorders (apathy, anxiety, depression, aggression). Although its etiology is not fully understood, there are several characteristics of the disease which play an important role in this pathology, as senile plaques (β-amyloid deposits derived from abnormal metabolism of the amyloid precursor protein), neurofibrillary tangles (comprised of abnormally hyperphosphorylated tau protein), oxidative damage to various cellular structures and low levels of the neurotransmitter acetylcholine.

Current treatments are fundamentally symptomatic. In recent decades, the cholinergic approach has placed four drugs on the market for treatment of the disease: acetylcholinesterase enzyme inhibitors (AChE) tacrine, donepezil, rivastigmine, and galantamine, which enhance neurotransmission in the cholinergic synapses of the brain, alleviating cognitive deficits (Villarroya, M. et al., *Expert Opin. Investig. Drugs* 2007, 16, 1987-1998). So far, the only drug approved of a noncholinergic nature is memantine, an N-methyl-D-aspartate antagonist, which increases memory and intellectual abilities by modulation of the glutamatergic system (Parsons, C. G. et al., *Neuropharmacology* 2007, 53, 699-723). Below are approved drugs for the treatment of AD:

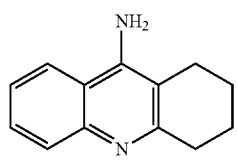

Tacrine

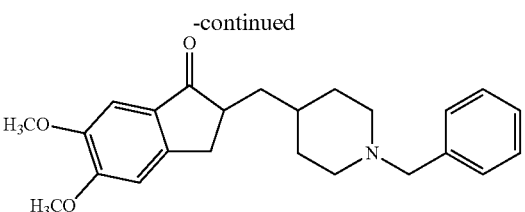

Donepezil

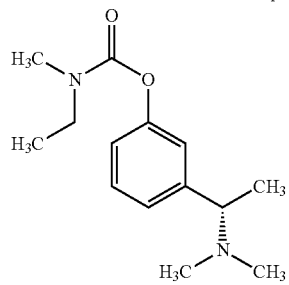

Rivastigmine

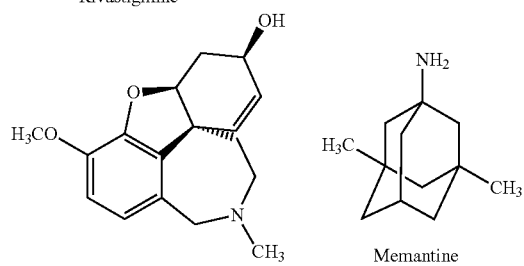

Galantamine                Memantine

The AChE enzyme has two major sites: the active catalytic center (CAS) where hydrolysis of acetylcholine is produced and where the bottom of a narrow throat is found and the peripheral anionic site (PAS) located in the catalytic throat inlet.

Apart from its role in cholinergic transmission, AChE has other functions related to neuronal differentiation, cell adhesion, and aggregation of the amyloid peptide. Different biochemical studies have revealed that AChE promotes the formation of aggregates of β-amyloid (Aβ), establishing AChE-Aβ complexes which are more toxic than the isolated Aβ itself. Since the point of attachment between the enzyme and the peptide is located on the PAS, the dual AChE inhibitors, capable of interacting simultaneously with CAS and PAS sites are of great interest in AD since they can ameliorate cognitive deficits and halt related the neurotoxicity of Aβ (Ferrari, G. V. et al., *Biochemistry* 2001, 40, 10447-10457). In recent years, various families of dual AChE inhibitors have been described (for example, Fernández-Bachiller, M. I. et al., *ChemMedChem* 2009, 4, 828-841; Muñoz-Torrero, D., *Curr. Med. Chem.* 2008, 15, 2433-2455).

The inhibition of monoamine oxidases has an interesting pharmacological property to be taken into account when designing new drugs for potential treatment of AD and Parkinson's, since during the deamination reaction of the neurotransmitter amines, such as adrenaline, dopamine and serotonin, catalyzed by MAOs, hydrogen peroxide is generated ($H_2O_2$), which is a source of oxygenated free radicals, highly toxic agents, and responsible for the oxidative stress that negatively affects the neurons in AD and Parkinson's (Schneider, L. S. et al. *Am. J. Psychiatry* 1993, 18, 321-323;

Marin, D. B. et al. *Psychiatry Res.* 1995, 58, 181-189; Alper, G. et al. *Eur. Neuropsychopharmacol.* 1999, 9, 247-252).

DESCRIPTION OF THE INVENTION

This invention concerns a series derived from N-methyl-N-{[(1-methyl-5-alcoxy)-1H-indol-2-yl]methyl}prop-2-yn-1-amine, that exhibit inhibitory activity of the monoamine oxidases A and B enzymes, acetylcholinesterase, and butyrylcholinesterase, involved in the biochemical processes related to the development of symptoms of some neurodegenerative diseases such as Alzheimer's disease or Parkinson's disease.

In a first aspect, this invention relates to a compound of formula (I)

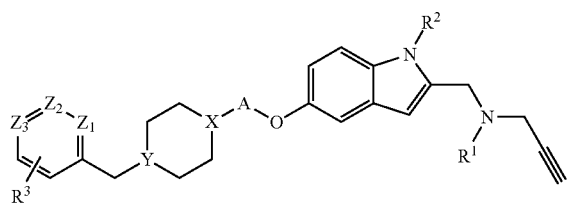

(I)

where,
$R^1$ and $R^2$ are selected from H and $C_1$-$C_{10}$ alkyl,
$R^3$ is selected from H, —$OR_4$, N, —CN, —C(O)$R_4$, —C(O)O$R_4$, —C(O)N$R_4R_5$, —C=N$R_4$, —OC(O)$R_4$, —N$R_4R_5$, —N$R_4$C(O)$R_5$, —$NO_2$, —N=C$R_4R_5$, halogen and $C_1$-$C_{10}$ alkyl,
where $R_4$ and $R_5$ are selected from H, alkyl, alkenyl, cycloalkyl and aryl,
X, Y, $Z_1$, $Z_2$ y $Z_3$ are selected independently from CH and N,
A is selected from $(CH_2)_n$, NH, O and CO, where n is a whole number from 1 to 6, or their salts, isomers or solvates The term "alkyl" refers to, in this invention, to linear or branched hydrocarbon chain radicals, having from 1 to 10 carbon atoms, preferably 1 to 4, and which bind to the rest of the molecule by a single bond, for example, methyl, ethyl, n-propyl, i-propyl, n-butyl, tert-butyl, sec-butyl, n-pentyl, n-hexyl, etc. The alkyl groups may be optionally substituted by one or more substituents such as halogen, hydroxyl, alkoxyl, carboxyl, carbonyl, cyano, acyl, alkoxycarbonyl, amino, nitro, mercapto, and alkylthio.

The term "alkenyl" refers to radicals of hydrocarbon chains containing one or more carbon-carbon double bonds, for example vinyl, 1-propenyl, allyl, isoprenyl, 2-butenyl, 1,3-butadienyl, etc. The alkyl radicals may be optionally substituted by one or more substituents such as halogen, hydroxyl, alkoxyl, carboxyl, cyano, carbonyl, acyl, alkoxycarbonyl, amino, nitro, mercapto, and alkylthio.

"Cycloalkyl" refers in this invention to a stable monocyclic or bicyclic radical of 3 to 10 members, which is saturated or partially saturated, and which consists only of carbon and hydrogen atoms, such as cyclopentyl, cyclohexyl or adamantyl, and which may be optionally substituted by one or more groups such as alkyl, halogen, hydroxyl, alkoxyl, carboxyl, cyano, carbonyl, acyl, alkoxycarbonyl, amino, nitro, mercapto and alkylthio.

The term "aryl" refers within this invention to a radical phenyl, naphthyl, indenyl, phenanthryl or anthracyl. The alkyl radical may be optionally substituted by one or more substituents such as alkyl, haloalkyl, aminoalkyl, dialkylamino, hydroxyl, alkoxy, phenyl, mercapto, halogen, nitro, cyano and alkoxycarbonyl.

In a preferred embodiment, where X and/or Y is CH.
In another preferred embodiment, $R_3$ is H.
In another preferred embodiment, $R^1$ and $R^2$ are independently a $C_1$-$C_4$ alkyl.
In another aspect, this invention relates to a compound of formula (II):

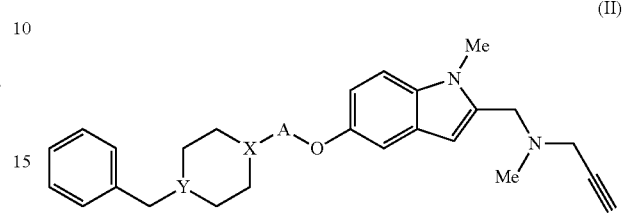

(II)

where X and Y are independently selected from CH and N, A is selected from $(CH_2)_n$, NH, O and CO, where n is a whole number from 1 to 6.
In a preferred embodiment, A is a $(CH_2)_n$ group, where n is a whole number from 1 to 4.
In another preferred embodiment, X is N.
In another preferred embodiment, Y is N.
In another aspect, this invention refers to a compound that is selected from the following list:
N-((5-(2-(4-benzylpiperidin-1-yl)ethoxy)-1-methyl-1H-indol-2-yl)methyl)-N-methylprop-2-yn-1-amine
N-((5-(3-(4-benzylpiperidin-1-yl)propoxy)-1-methyl-1H-indol-2-yl)methyl)-N-methyl prop-2-yn-1-amine
N-((5-(3-(4-benzylpiperazine-1-yl)propoxy)-1-methyl-1H-indol-2-yl)methyl)-N-methyl prop-2-yn-1-amine
N-((5-((1-benzylpiperidin-4-yl)methoxy)-1-methyl-1H-indol-2-yl)methyl)-N-methyl prop-2-yn-1-amine.
N-((5-(2-(1-benzylpiperidin-4-yl)ethoxy)-1-methyl-1H-indol-2-yl)methyl)-N-methyl prop-2-yn-1-amine
N-((5-(3-(1-benzylpiperidin-4-yl)propoxy)-1-methyl-1H-indol-2-yl)methyl)-N-methyl prop-2-yn-1-amine.
N-((5-(4-(1-benzylpiperidin-4-yl)butoxy)-1-methyl-1H-indol-2-yl)methyl)-N-methyl prop-2-yn-1-amine.
or their salts, isomers or solvates.
An additional preferred embodiment refers to the following compounds:
Dihydrochloride of N-((5-(2-(4-benzylpiperidin-1-yl)ethoxy)-1-methyl-1H-indol-2-yl)methyl)-N-methylprop-2-yn-1-amine
Dihydrochloride of N-((5-(3-(4-benzylpiperidin-1-yl)propoxy)-1-methyl-1H-indol-2-yl)methyl)-N-methylprop-2-yn-1-amine
Trihydrochloride of N-((5-(3-(4-benzylpiperidin-1-yl)propoxy)-1-methyl-1H-indol-2-yl)methyl)-N-methylprop-2-yn-1-amine.
Dihydrochloride of N-((5-((1-benzylpiperidin-4-yl)methoxy)-1-methyl-1H-indol-2-yl)methyl)-N-methylprop-2-yn-1-amine.
Dihydrochloride of N-((5-(2-(1-benzylpiperidin-4-yl)ethoxy)-1-methyl-1H-indol-2-yl)methyl)-N-methylprop-2-yn-1-amine
Dihydrochloride of N-((5-(3-(1-benzyl piperidin-4-yl)propoxy)-1-methyl-1H-indol-2-yl)methyl)-N-methylprop-2-yn-1-amine
Dihydrochloride of N-((5-(4-(1-benzyl piperidin-4-yl)butoxy)-1-methyl-1H-indol-2-yl)methyl)-N-methylprop-2-yn-1-amine
or their isomers.

The compounds of the present invention represented by the formula (I) may include isomers, depending on the presence of multiple bonds (for example Z, E), including optical isomers or enantiomers, depending on the presence of chiral centers. The individual isomers, enantiomers, or diastereoisomers and mixtures thereof fall within the scope of this invention, i.e., the isomer term also refers to any mixture of isomers, as diastereomers, racemates, etc., including their optically active isomers or mixtures in various proportions thereof. The individual enantiomers or diastereoisomers, as well as their mixtures, may be separated by conventional techniques.

In another aspect, this invention relates to a pharmaceutical composition comprising at least one compound of formula (I) as defined above and at least one adjuvant, excipient and/or pharmaceutically acceptable carrier. In another preferred embodiment, this composition further comprises another active ingredient.

For its application in therapy, the compounds of formula (I), salts or isomers thereof, will preferably be found in a pharmaceutically acceptable or substantially pure form, i.e., having a pharmaceutically acceptable level of purity excluding normal pharmaceutical additives such as diluents and carriers, and including no material considered toxic at normal dosage levels. The purity levels for the active ingredient are preferably above 50%, more preferably above 70%, and still more preferably above 90%. In a preferred embodiment, they are above 95% of the compound of formula (I).

The pharmaceutically acceptable adjuvants and carriers that may be used in said compositions are the adjuvants and carriers known by those skilled in the art and habitually used in the preparation of therapeutic compositions.

In another particular embodiment, said pharmaceutical composition is prepared in a solid form or an aqueous suspension, in a pharmaceutically acceptable diluent. The therapeutic composition provided by this invention can be administered via any appropriate route of administration, for which said composition will be formulated in the proper pharmaceutical form for the chosen route of administration. In a particular embodiment, administration of the therapeutic composition provided by this invention is carried out by oral, topical, rectal or parenteral (including subcutaneous, intraperitoneal, intradermal, intramuscular, intravenous, etc.) route.

In another aspect, this invention relates to the use of a compound of formula (I) as described above for the manufacture of a medication.

In another aspect, this invention relates to the use of a compound of formula (I) as described above for the manufacture of a medication for treatment of a neurodegenerative disease.

In a preferred embodiment, the neurodegenerative disease is selected from senile dementia, cerebrovascular dementia, mild cognitive impairment, attention deficit disorders, neurodegenerative diseases associated with aberrant protein aggregations as Parkinson's disease or Alzheimer's disease, amyotrophic lateral sclerosis, prion diseases such as Creutzfeldt-Jakob disease or Gerstmann-Straussler-Scheinker. In an even more preferred embodiment, the neurodegenerative disease is Parkinson's disease or Alzheimer's disease.

The use of the compounds of the invention is compatible with their use in protocols wherein the compounds of formula (I), or mixtures thereof are used by themselves or in combination with other treatments or medical procedures.

One aspect of the present invention relates to a method of obtaining a compound of formula (I) which comprises the reaction of a compound of formula (III)

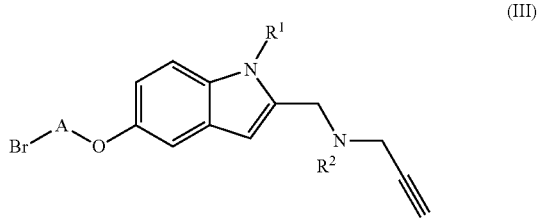

(III)

where $R^1$, $R^2$ and A are as defined above,
with a compound of formula (IV):

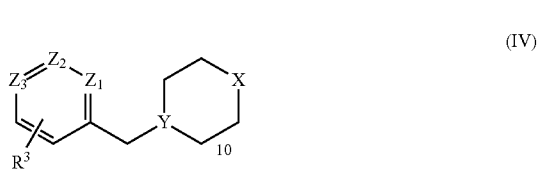

(IV)

where $R^3$, X, Y and $Z_1$, $Z_2$ and $Z_3$ are as defined above.

Another aspect of the present invention relates to a method of obtaining a compound of formula (I) which comprises the reaction of a compound of formula (V):

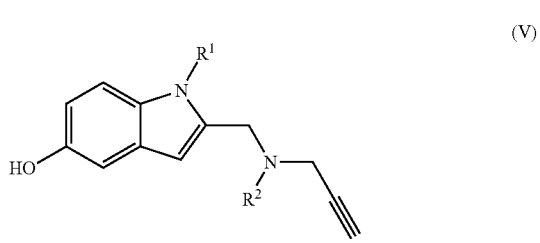

(V)

where $R^1$, $R^2$ are as defined above,
and a compound of formula (VI):

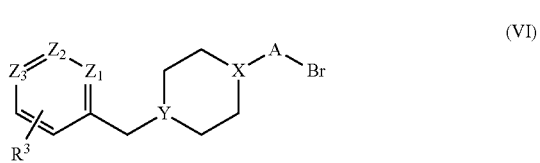

(VI)

where $R^3$, A, X, Y, $Z_1$, $Z_2$ and $Z_3$ are as defined above.

Throughout the description and claims the word "comprise" and its variants do not intend to exclude other technical features, additives, components or steps. For those skilled in the art, other objects, advantages and features of the invention will emerge partly from the description and partly from the practice of the invention. The following examples and drawings are provided as a way to illustrate and are not intended to limit this invention.

EXAMPLES

The invention will be illustrated below by means of tests made by the inventors, which show the specificity and effectiveness of the compounds of formula (I) of the invention.

1. Synthesis of Compounds of Formula (I)

All the anhydrous solvents were distilled using a Pure sols solvent purification system model PS-400-3-MD. The melting points (not corrected), and measured on a Kofler-type microscope (Reichert Jung Thermovar). The $^1$H-NMR and $^{13}$C NMR spectra were performed on a Varian Inova-300 (300 MHz), Mercury-400 (400 MHz), Varian Inova-400 (400 MHz) and Unity-500 (500 MHz). Chemical shifts (in ppm) are referenced to the residual solvent signal used [CDCl3: 7.27 (D), 77.2 (C) ppm; CD3OD: 4.84 (d), 49.05 (C) ppm]. The multiplicity of signals (s, singlet; d, doublet; t, triplet; c: quartet, q, quintet, m, multiplet), number of protons (deducted by integration), the value of the coupling constants J (in hertz) and the structural assignment inferred from studying bidimensional experiments ($^1$H, $^1$H-COSY, $^1$H, $^{13}$C-HSQC, $^1$H, $^{13}$C-HMBC). Mass spectra were recorded on an LC/MS HP-1100MSD spectrometer with APCI and API-ES ionization sources. Also, in the cases, the spectra were recorded by electron impact on a sample injection HP-5873MSD spectrometer by direct probe. Infrared spectra were obtained on a Perkin-Elmer Spectrum One on a KBr pellet. The most significant bands are indicated in cm$^{-1}$. The elemental analyzes were performed with a Heraus CHN-O Rapid analyzer and are expressed in percentages. Chromatographic separations were performed by column chromatography using Merck silica gel 60 (0.063-0200 nm) under pressure (flash) and in gradient, using as an eluent, the mixtures detailed in each case, or by chromatotron (accelerated centrifugal radial chromatography) model 7924 with Merck silica gel plates 60 $F_{254-366}$. For thin layer chromatography PL Merck F244 silica gel chromatofolios were used.

1.1. Synthesis of 5-(2-bromoethoxy)indole (9)

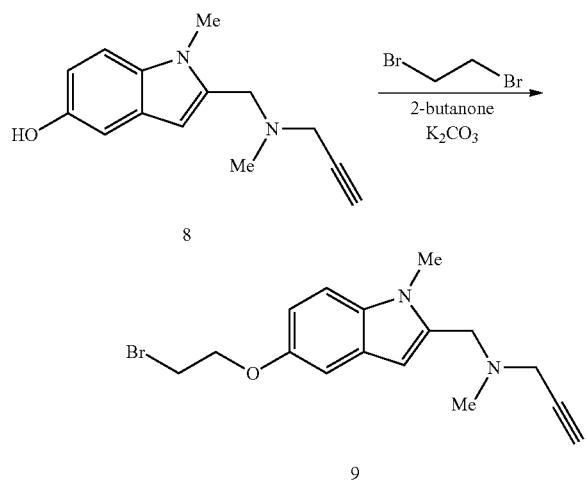

A solution of 1-methyl-2-{[methyl(prop-2-yn-1-yl)amino]methyl}-1H-indol-5-ol (8) (Cruces, M. A.; Elorriaga, C.; Fernández-Álvarez, E. *Eur. J. Med. Chem.* 1991, 26, 33-41) (0.215 g, 0.942 mmol), 1,2-dibromoethane (1.77 g, 9.42 mmol), and potassium carbonate (0.65 g, 4.71 mmol) in 2-butanone (8 mL) was heated at 85° C. for 6 h. The mixture was evaporated under vacuum and the residue was extracted with dichloromethane (10 mL) and water (10 mL). The organic phase was dried (Na$_2$SO$_4$) and evaporated. The residue was purified by column chromatography, eluting with a 4% methanol mixture in dichloromethane to give compound 9 (117.3 mg, 37%). R$_f$=0.76 (CH$_2$Cl$_2$/AcOEt, 10/1); pf 75-77° C.; RMN of $^1$H (300 MHz, CDCl$_3$) δ 2.31 (t, J=2.4 Hz, 1H, ≡CH), 2.36 (s, 3H, N—CH$_3$), 3.32 (d, J=2.4 Hz, 2H, N—CH$_2$—C≡), 3.66 (t, J=6.4 Hz, 2H, —CH$_2$—Br), 3.69 (s, 2H, N—CH$_2$), 3.75 (s, 3H, N—CH$_3$), 4.33 (t, J=6.4 Hz, 2H, —CH$_2$—O—), 6.36 (s, 1H, CH$_3$), 6.9 (dd, J=8.8, 2.5 Hz, 1H, CH$_6$), 7.07 (d, J=2.4 Hz, 1H, CH$_4$), 7.2 (d, J=8.8 Hz, 1H, CH7); RMN of $^{13}$C (75 MHz, CDCl$_3$) δ 29.6 (CH$_2$—Br), 29.9 (N—CH$_3$), 41.5 (N—CH$_3$), 44.7 (—CH$_2$—C≡), 51.7 (CH$_2$—N), 69.1 (CH$_2$—O), 73.5 (≡CH), 78.3 (—C≡), 102.15 (CH3ind), 104.42 (CH4ind), 109.7 (CH7$_{ind}$), 112.2 (CH6ind), 127.4 (C3aind), 133.8 (C7aind), 137.3 (C2ind), 152.2 (C5ind); EM (IE) m/z (%): 131 (48), 160 (66) [M-((Br(CH$_2$)$_2$)—NCH$_3$CH$_2$C≡CH)]$^+$, 267 (100) [M-NCH$_3$CH$_2$C≡CH)]$^+$, 334 (25)[M]$^+$

1.2. Synthesis of dihydrochloride of N-{(5-[2-(4-benzylpiperidin-1-yl)ethoxy)-1-methyl-1H-indol-2-yl]methyl}-N-methylprop-2-yn-1-amine (1)

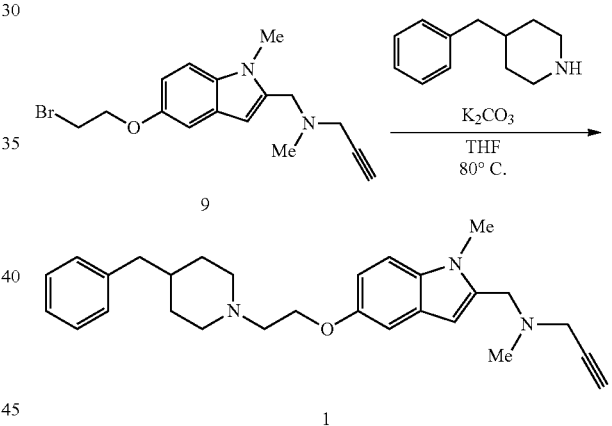

Commercial 4-benzylpiperidine (36 μl, 0.2 mmol) was added to a suspension of 9 (34 mg, 0.1 mmol) and potassium carbonate (42 mg, 0.3 mmol) in DMF (1 mL). The mixture was heated at 80° C. overnight in an argon environment. The mixture was cooled, and it was poured over water (5 mL), and was extracted with dichloromethane (3×20 mL). The organic phase was dried (Na$_2$SO$_4$) and vacuum evaporated. The residue was purified by column chromatography, eluting with a 3.3% methanol mixture in dichloromethane to give compound 1 (33.5 mg, 77%). R$_f$=0.49 (CH$_2$Cl$_2$/MeOH, 10/1); RMN of $^1$H (400 MHz, CDCl$_3$) δ 1.38 (qd, J=12.1 and 3.7 Hz, CH$_2$), 1.56 (m, CH), 1.67 (d, J=12.8 Hz, CH$_2$), 2.08 (td, J=11.7, 2.1 Hz, 1H, CH$_2$), 2.31 (t, J=2.3 Hz, C≡CH), 2.35 (s, 3H, CH$_3$), 2.56 (d, J=7.0 Hz, CH$_2$), 2.83 (t, J=6.0 Hz, CH$_2$), 3.034 (d, J=11.7 Hz, CH$_2$), 3.32 (d, J=2.3 Hz, 2H, CH$_2$), 3.68 (s, 2H, N—CH$_2$), 3.74 (s, 3H, CH$_3$), 4.16 (t, J=6.0 Hz, 2H, —CH$_2$—O), 6.35 (s, 1H, CH), 6.88 (dd, J=8.8 and 2.4 Hz, 1H), 7.06 (d, J=2.3 Hz, 1H), 7.14-7.23 (m, 4H), 7.25-7.31 (m, 2H); RMN of $^{13}$C (100 MHz, CDCl$_3$) δ 29.8 (CH$_3$), 32.0 (2×CH$_2$), 37.6 (CH), 41.5 (NCH$_3$), 43.1 (CH$_2$), 44.6 (CH$_2$), 51.7 (CH₂-indol), 54.2 (2×CH₂), 57.6 (CH₂), 66.6 (CH₂—O), 73.4 (—C≡), 78.3 (≡CH), 102.0 (CH3ind), 103.4 (CH4ind), 109.5 (CH7ind), 111.0 (CH6ind), 125.7 (CHPh), 127.4 (C3aind), 128.0 (2×CH$_{Ph}$), 129.0 (2×CH$_{Ph}$), 133.3 (C7aind), 137.0 (C2ind), 140.60 (C1'Ph), 152.96 (C5ind); EM (IE) m/z (%): 188 (100), 202 (42), 429 (6)[M]$^+$ (1.2× HCl): pf 218-220° C.; IR (KBr) v 3421, 3189, 2929, 2498, 1619, 1486, 1208, 1163 cm$^{-1}$. Anal. Calcd. for C$_{28}$H$_{37}$Cl$_2$N$_3$O+⅔H$_2$O: C, 65.36; H, 7.51; N, 8.17; Cl, 13.78. Found: C, 65.08; H, 7.74; N, 8.40; Cl, 12.34.

1.3. Synthesis of 5-(3-bromopropoxy)indole (10)

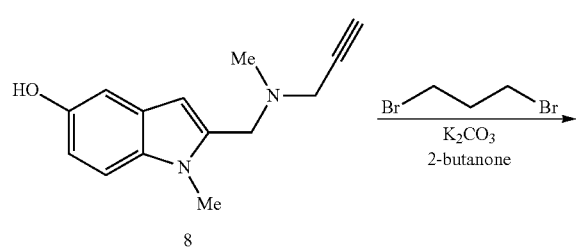

Following the same procedure as for the synthesis of Compound 9,1-methyl-2-{[methyl(prop-2-yn-1-yl)amino]metal}-1H-indol-5-ol 8 (Cruces, M. A.; Elorriaga, C.; Fernández-Álvarez, E. Eur. J. Med. Chem. 1991, 26, 33-41) (21 mg, 0.092 mmol), was transformed into product 10 (25.4 mg, 80%). R$_f$=0.62 (CH₂Cl₂/AcOEt, 10/1); pf 71-72° C.; IR (KBr) v 3275, 1488, 1468, 1206, 1026 cm$^{-1}$; RMN of $^1$H (400 MHz, CDCl₃) δ 2.30 (t, J=2.4 Hz, 1H, ≡CH), 2.33 [t, J=5.9 Hz, CH₂—(CH₂O)], 2.36 (s, 3H, N—CH₃), 3.32 (d, J=2.4 Hz, 2H, CH₂—C≡), 3.65 (t, J=6.5 Hz, 2H, —CH₂—Br), 3.69 (s, 2H, ind-CH₂—N), 3.75 (s, 3H, N—CH₃), 4.14 (t, J=5.8 Hz, 2H, —CH₂—OH), 6.35 (s, 1H, CH3), 6.87 (dd, J=8.8, 2.4 Hz, 1H, CH6), 7.07 (d, J=2.4 Hz, 1H, CH4), 7.2 (d, J=8.9 Hz, 1H, CH7); RMN of $^{13}$C (100 MHz, CDCl₃) δ 29.8 (N—CH₃), 30.3 (CH₂—Br), 32.6 (CH₂—(CH₂O), 41.5 (N—CH₃), 44.6 (CH₂—C≡), 51.7 (CH₂—N), 66.3 (CH₂—O), 73.4 (≡CH), 78.3 (—C≡), 102.1 (CH3ind), 103.6 (CH4ind), 109.6 (CH7ind), 111.9 (CH6ind), 127.2 (C3aind), 133.5 (C7aind), 137.1 (C2ind), 152.8 (C5ind); EM (IE) m/z (%): 131 (60), 160 (100) [M-((Br(CH₂)₃)—CH₃NCH₂C≡CH)]$^+$, 227 (7) [M-(Br(CH₂)₃)]$^+$, 281 (96) [CH₃NCH₂C≡CH)]$^+$, 348 (21)[M]$^+$. Anal. Calcd. by (C₁₇H₂₁BrN₂O) (348,0837): C, 58.46; H, 6.06; Br, 22.88; N, 8.02. Found: C, 58.49; H, 6.08; N, 22.11; N, 8.23.

1.4. Synthesis of dihydrochloride of N-{(5-[3-(4-benzylpiperidin-1-yl)propoxy)-1-methyl-1H-indol-2-yl]methyl}-N-methylprop-2-yn-1-amine (2)

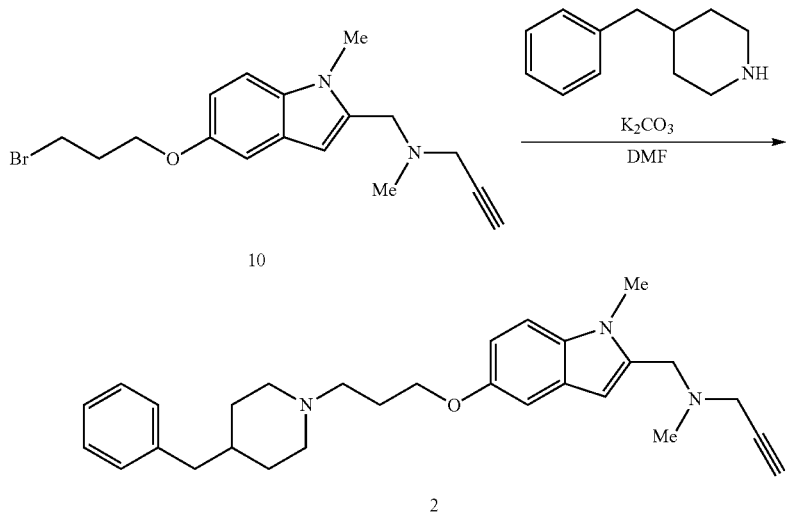

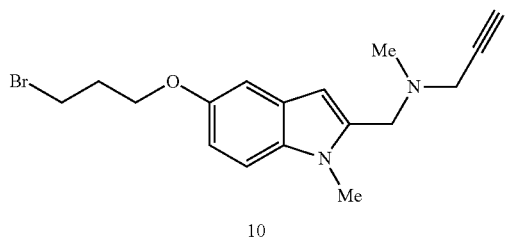

Following the same procedure as for the preparation of compound 2, starting from commercial 4-benzylpiperidine (0.11 mL, 0.63 mmol, 2 equiv) and compound 10 (111 mg, 0.31 mmol, 1 equiv), product 2 was obtained (89.2 mg, 64%): R$_f$=0.43 (CH₂Cl₂/MeOH, 10/1); pf 82-83° C.; IR (KBr) v 3274, 2923, 1619, 1487, 1469, 1390, 1205, 1133, 1027 cm$^{-1}$; RMN of $^1$H (400 MHz, CDCl₃) δ 1.40 (qd, J=12.1, 3.2 Hz, CH₂), 1.55 (m, CH), 1.66 (d, J=12.7 Hz, CH₂), 1.92-2.08 (m, 4H, 2×CH₂), 2.29 (t, J=2.3 Hz, C≡CH), 2.34 (s, 3H, CH₃), 2.55 (d, J=6.7 Hz, CH₂), 2.59 (t, J=7.3 Hz, CH₂), 3.02 (d, J=11.4 Hz, CH₂), 3.30 (d, J=2.3 Hz, 2H, CH₂), 3.67 (s, 2H, CH₂—N), 3.73 (s, 3H, CH₃), 4.03 (t, J=6.2 Hz, 2H, —CH₂—O), 6.32 (s, 1H, CH3ind), 6.83 (dd, J=8.8, 2.4 Hz, 1H, CH6ind), 7.02 (d, J=2.2 Hz, 1H, CH4ind), 7.12-7.21 (m, 4H), 7.25-7.31 (m, 2H); RMN of $^{13}$C (100 MHz, CDCl₃) 26.7 (CH₂), 29.8 (CH₃), 31.7 (2×CH₂), 37.7 (CH), 41.5 (N—CH₃), 43.0 (CH₂), 44.7 (CH₂), 51.7 (CH₂), 53.8

(2×CH$_2$), 55.7 (CH$_2$), 67.2 (CH$_2$—O), 73.4 (—C≡), 78.3 (≡CH), 102.0 (CH3ind), 103.4 (CH4ind), 109.5 (CH7ind), 111.9 (CH6ind), 125.7 (CHPh), 127.4 (C3aind), 128.1 (2×CHPh), 129.0 (2×CHPh), 133.3 (C7aind), 137.0 (C2ind), 140.5 (C1'Ph), 153.1 (C5ind); EM (ES) m/z (%): 188 (99), 444 (100) [M+H]$^+$, 445 (40) [M+2H]$^+$, 466 (2)[M+Na]$^+$. Anal. Calcd. for (C$_{29}$H$_{37}$N$_3$O) (348,0837): C, 78.51; H, 8.41; N, 9.47.

Found: C, 78.63; H, 8.59; N, 9.44.

2. 2×HCl: pf 216-218° C.; IR (KBr) 3196, 2931, 2559, 2509, 1619, 1485, 1472, 1454, 1250, 1211, 1162 cm$^{-1}$.

1.5. Synthesis of trihydrochloride of N-{(5-[3-(4-benzylpiperazin-1-yl)propoxy)-1-methyl-1H-indol-2-yl]methyl}-N-methylprop-2-yn-1-amine (3)

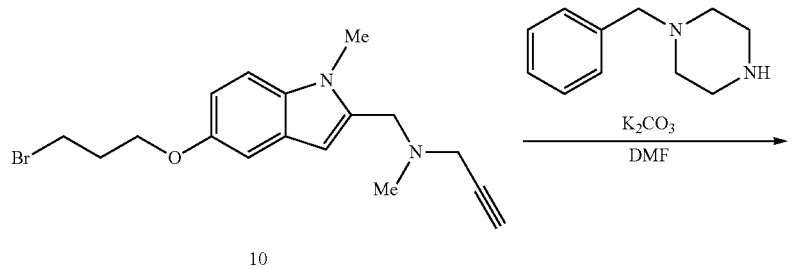

10

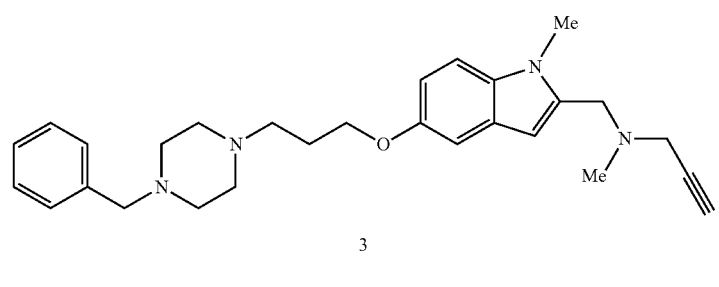

3

Following the same procedure, but starting from commercial 1-benzylpiperazine (0.148 g, 0.845 mmol) and 5-(3-bromopropoxy)-indole (10) (0.147 g, 0.422 mmol) the product 3 was obtained (0.16 g, 85%). R$_f$=0.43 (CH$_2$Cl$_2$/MeOH, 10/1); pf 103-4° C.; IR (KBr) v 3138, 2958, 2943, 2806, 2762, 1621, 1492, 1480, 1207, 1159, 1003 cm$^{-1}$; RMN of $^1$H (400 MHz, CDCl$_3$) δ 2.01 [m, 2H, CH$_2$(CH$_2$O)], 2.32 (t, J=2.3 Hz, 1H, C≡CH), 2.36 (s, 3H, N—CH$_3$), 2.53 (m, 8H, 4×CH$_2$), 3.33 (d, J=2.3 Hz, 2H, CH$_2$C), 3.54 (s, 2H, CH$_2$—N), 3.69 (s, 2H, CH$_2$Ph), 3.75 (s, 3H, N—CH$_3$), 4.06 (t, J=6.4 Hz, 2H, —CH$_2$O), 6.35 (s, 1H, CH3ind), 6.88 (dd, J=8.8, 2.4 Hz, 1H, CH6ind), 7.07 (d, J=2.4 Hz, 1H, CH4ind), 7.19 (d, J=8.8 Hz, 1H, CH7ind) 7.25-7.37 (m, 5H); RMN of $^{13}$C (100 MHz, CDCl$_3$) 26.9 [CH$_2$(CH$_2$O)], 29.8 (N—CH$_3$), 41.5 (N—CH$_3$), 44.6 (CH$_2$), 51.7 (CH$_2$), 53.0 (2×CH$_2$), 53.1 (CH$_2$), 55.3, 63.0, 67.1 (CH$_2$—O), 73.4 (—C≡), 78.3 (≡CH), 101.9 (CH$^3_{ind}$), 103.2 (CH4ind), 109.5 (CH7ind), 111.9 (CH6ind), 126.9 (CHPh), 127.4 (C3aind), 128.1 (2×CHPh), 129.1 (2×CHPh), 133.2 (C7aind), 136.9 (C2ind), 138.0 (C1'Ph), 153.1 (C5ind); EM (ES) m/z (%): 445 (100) [M+H]$^+$, 467 (2) [M+Na]$^+$. Anal. Calcd. for (C$_{28}$H$_{36}$N$_4$O): C, 75.64; H, 8.16; N, 12.60.

Found: C, 75.39; H, 8.40; N, 12.52.

3. 3×HCl: pf 227-230° C.; IR (KBr) v 3195, 2953, 2561, 2516, 2442, 1620, 1485, 1472, 1442, 1211, 1163 cm$^{-1}$. Anal. Calcd. for (C$_{28}$H$_{39}$Cl$_3$N$_4$O+½(H$_2$O)) (561.21): C, 59.73; H, 7.16; N, 9.95; Cl, 18.89. Found: C, 59.59; H, 7.49; N, 10.20; Cl, 18.53.

1.6. Synthesis of dihydrochloride of N-{(5-((1-benzylpiperidin-4-yl)methoxy)-1-methyl-1H-indol-2-yl)methyl}-N-methylprop-2-yn-1-amine (4)

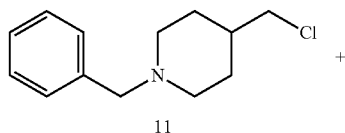

11

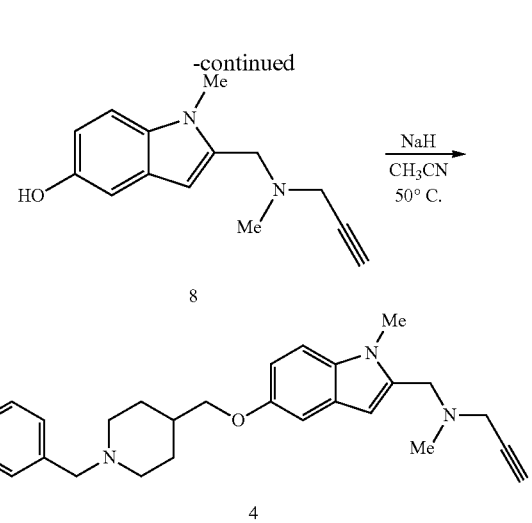

A dissolution of 1-methyl-2-{[methyl(prop-2-yn-1-yl)amino]methyl}-1H-indol-5-ol. 8 (Cruces, M. A.; Elorriaga, C.; Fernández-Álvarez, E. Eur. J. Med. Chem. 1991, 26, 33-41) (0.21 g, 0.94 mmol) and 1-benzyl-4-(chloromethyl) piperidine 11 (Mohapatra, P. P.; Bhat, L. WO2008073452 (0.33 g, 1.51 mmol, 1.5 equiv) in dry acetonitrile (5 mL) NaH (60%) (120 mg, 3 equiv) (previously washed with dry hexane) was added in several portions. The mixture was heated at 50° C. for 10 h in an argon environment. The solvent was evaporated and the residue was diluted with dichloromethane. The mixture was washed with water and extracted with dichloromethane (3×20 mL). The organic phase was dried ($Na_2SO_4$) and vacuum evaporated. The residue was purified by column chromatography, eluting with a 1% methanol mixture in dichloromethane to give compound 4 (126.3 mg, 32%). $R_f$=0.24 ($CH_2Cl_2$/MeOH, 10/1); pf 123-5° C.; IR (KBr) ν 3252, 2938, 2913, 1620, 1489, 1466, 1195, 1163, 1029, 1008 $cm^{-1}$; RMN DE $^1H$ (400 MHz, $CDCl_3$) δ 1.39-1.49 (m, 2H), 1.81-1.91 (m, 3H), 2.02 (t, J=16 Hz, 2H), 2.30 (t, J=2.2 Hz, C≡CH), 2.35 (s, 3H, N—$CH_3$), 2.95 (d, J=11.4 Hz, 2H), 3.31 (d, 2H, J=2.2 Hz, $CH_2$—C≡CH), 3.53 (s, 2H, $CH_2$-Ph), 3.68 (s, 2H, ind-$CH_2$—N), 3.73 (s, 3H, N—$CH_3$), 3.85 (d, J=6.0 Hz, 2H, O—$CH_2$—), 6.34 (s, 1H, CH-3), 6.86 (dd, J=8.8, 2.3 Hz, 1H, CH-6), 7.04 (d, J=2.3 Hz, 1H, CH-4), 7.18 (d, J=8.8 Hz, 1H, CH-7), 7.24-7.35 (m, 5H); RMN of $^{13}C$ (100 MHz, $CDCl_3$) 29.1 (2×$CH_2$), 29.8 (ind-$CH_3$), 35.9 (CH-piperidine), 41.5 (N—$CH_3$), 44.6 ($CH_2$—C≡), 51.7 (Ind-$CH_2$—N), 53.4 (2×$CH_2$), 63.4 (Ph-$CH_2$), 54.0 (2×$CH_2$), 63.4 ($CH_2$-Ph), 73.4 (≡CH), 73.6 ($CH_2$—O), 78.4 (—C≡), 102.0 (CH3ind), 103.3 (CH4ind), 109.5 (CH7ind), 111.9 (CH6ind), 126.8 (CH4'Ph), 127.5 (C3aind), 128.1 (2×CHPh), 129.1 (2×CHPh), 133.3 (C7aind), 137.8 (C2ind), 138.3 (C1'Ph), 153.3 (C5ind); EM (ES) m/z (%): 416 (100) $[M+H]^+$, 438 (2) $[M+Na]^+$.

4.2×HCl: pf 230-3° C.; IR (KBr) ν 3423, 3200, 2933, 2511, 1620, 1486, 1466, 1208, $cm^{-1}$. Anal. Calcd. for $C_{27}H_{35}Cl_2N_3O$: C, 66.39; H, 7.22; N, 8.60; Cl, 14.52. Found: C, 66.21; H, 7.43; N, 8.63; Cl, 14.42.

1.7. Synthesis of dihydrochloride of N-((5-(2-(1-benzylpiperidin-4-yl)ethoxy)-1-methyl-1H-indol-2-yl)methyl)-N-methylprop-2-yn-1-amine (5)

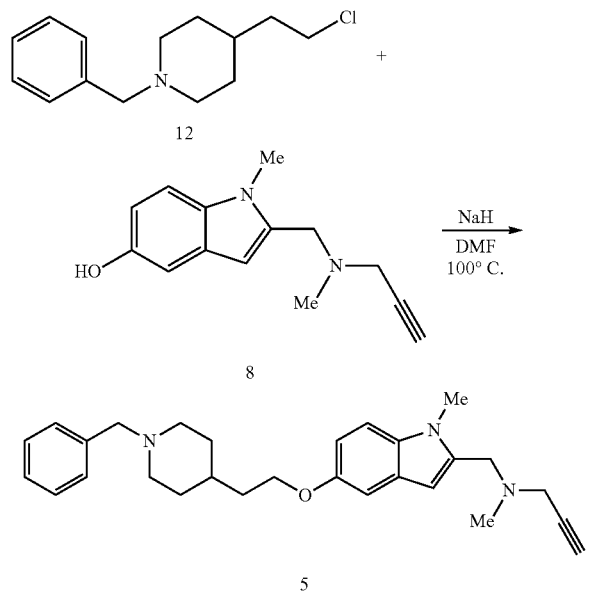

Following the same procedure, but starting from 1-benzyl-4-(2-chloroethyl)piperidine 12 (Contreras, J.-M.; Parrot, I.; Sippl, W.; Rival, Yveline M.; Wermuth, C. G. J. Med. Chem. 2001, 44, 2707-2718) (0.25 g, 1.05 mmol, 1.5 equiv) and 1-methyl-2-{[methyl(prop-2-yn-1-yl)amino]methyl}-1H-indol-5-ol. 8 (Cruces, M. A.; Elorriaga, C.; Fernández-Álvarez, E. Eur. J. Med. Chem. 1991, 26, 33-41) (160 mg, 0.7 mmol) in dry DMF (5 mL), product 5 was obtained (0.216 g, 72%): $R_f$=0.27 ($CH_2Cl_2$/MeOH, 10/1); pf 86-7° C.; RMN of $^1H$ (400 MHz, $CDCl_3$) δ 1.31-1.41 (m, 2H), 1.52-162 (m, CH), 1.72-1.77 (m, 4H), 2.0 (t, J=10.8, 2H), 2.29 (t, J=2.3 Hz, C≡CH), 2.34 (s, 3H, N—$CH_3$), 2.91 (d, J=11.6 Hz, 2H), 3.31 (d, 2H, J=2.3 Hz, $CH_2$—C≡CH), 3.52 (s, 2H, $CH_2$-Ph), 3.67 (s, 2H, N—$CH_2$), 3.74 (s, 3H, N—$CH_3$), 4.03 (t, J=6.5 Hz, 2H, O—$CH_2$—), 6.33 (s, 1H, CH-3), 6.85 (dd, J=8.8, 2.4 Hz, 1H, CH-6), 7.03 (d, J=2.4 Hz, 1H, CH-4), 7.18 (d, J=8.8 Hz, 1H, CH-7), 7.23-7.34 (m, 5H); RMN of $^{13}C$ (100 MHz, $CDCl_3$) δ 0.1 (N—$CH_3$), 32.4 ($CH_2$), 32.8 ($CH_2$), 36.2 ($CH_2$), 41.8 (N—$CH_3$), 44.9 ($CH_2$—C CH), 52.0 ($CH_2$-ind), 53.9 (2×$CH_2$), 63.6 ($CH_2$-Ph), 66.7 ($CH_2$—O), 73.68 (≡CH), 78.6 (—C≡), 102.0 (CH3ind), 103.5 (CH4ind), 109.5 (CH7ind), 112.2 (CH6ind), 127.2 (CHPh), 127.7 (C3aind), 128.3 (2×$CH_{Ph}$), 129.5 (2×CHPh), 133.6 (C7aind), 137.2 (C2ind), 138.4 (C1'Ph), 153.5 (C5ind); EM (IE) m/z (%): 91 (48) $[PhCH_2]^+$, 202 (100), 361 (3) $[M-NCH_3CH_2C≡CH)]^+$, 429 (4) $[M]^+$. Anal. Calcd. for ($C_{28}H_{35}N_3O$) (429, 2780): C, 78.28; H, 8.21; N, 9.78.

Found: C, 77.99; H, 8.45; N, 9.79.

5.2×HCl: pf 221-3° C.; IR (KBr) ν 3424, 3195, 2928, 2561, 2506, 1619, 1486, 1471, 1210, $cm^{-1}$. Anal. Calcd. for $C_{28}H_{37}Cl_2N_3O+\frac{1}{3}H_2O$: C, 66.13; H, 7.47; N, 8.26; Cl, 13.94. Found: C, 66.04; H, 7.89; N, 8.59; Cl, 13.84.

1.8. Synthesis of dihydrochloride of N-((5-[3-(1-benzylpiperidin-4-yl)propoxy)-1-methyl-1H-indol-2-yl)methyl)-N-methylprop-2-yn-1-amine (6)

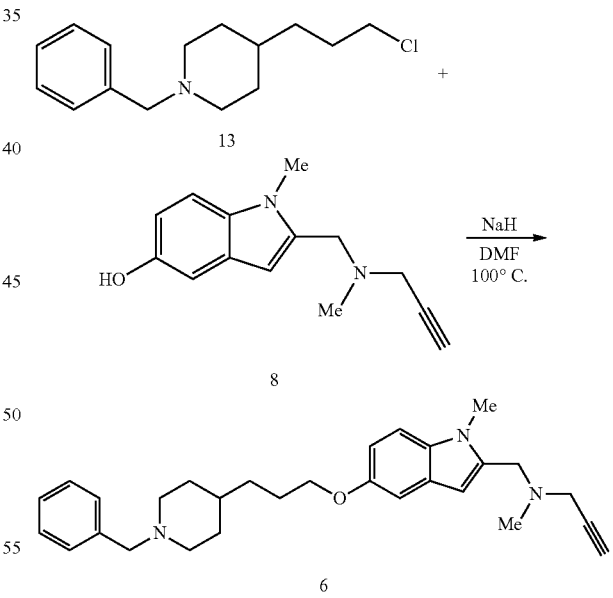

Following the same procedure, but starting from 1-benzyl-4-(3-chloropropyl)piperidine 13 (0.36 g, 1.44 mmol, 1.5 equiv) and 1-methyl-2-{[methyl(prop-2-yn-1-yl)amino]methyl}-1H-indol-5-ol. 8 (Cruces, M. A.; Elorriaga, C.; Fernández-Álvarez, E. Eur. J. Med. Chem. 1991, 26, 33-41) (0.22 g, 0.96 mmol) in dry DMF (5 mL), product 6 was obtained (0.268 g, 63%): $R_f$=0.28 ($CH_2Cl_2$/MeOH, 20/1); pf 90-1° C.; IR (KBr) ν 3265, 2935, 2908, 2799, 2760, 1619, 1489, 1471, 1395, 1269, 1204, 1190, 1160, 1029 $cm^{-1}$; RMN of $^1H$ (400

MHz, CDCl₃) δ 1.29-1.31 (m, 3H, CH+CH₂), 1.41-1.46 (m, 2H, CH₂—(CH₂)₂O), 1.72 (d, J=9.1 Hz, 2H, CH₂), 1.83 (m, 2H, CH₂—CH₂O), 1.97 (t, J=12 Hz, 2H, CH₂), 2.31 (t, J=2.0 Hz, C≡CH), 2.36 (s, 3H, N—CH₃), 2.91 (d, J=10.8 Hz, CH₂), 2.33 (d, J=2.2 Hz, 2H, CH₂—C≡CH), 3.52 (s, 2H, CH₂-Ph), 3.69 (s, 2H, ind-CH₂), 3.75 (s, 3H, ind-CH₃), 3.98 (t, J=6.6 Hz, 2H, O—CH₂—), 6.35 (s, 1H, CH-3), 6.85 (dd, J=8.8 and 2.3 Hz, 1H, CH-6), 7.05 (d, J=2.14 Hz, 1H, CH-4), 7.19 (d, J=8.8 Hz, 1H, CH-7), 7.25-7.35 (m, 5H, Ph); RMN of ¹³C (100 MHz, CDCl₃) δ 26.7 (CH₂—CH₂O), 29.8 (ind-N—CH₃), 32.2 (2CH₂), 32.8 [CH₂—(CH₂)₂O], 35.5 (CH-piperidine), 41.5 (N—CH₃), 44.6 (CH₂—C), 51.7 (ind-CH₂), 53.8 (2×CH₂), 63.4 (CH₂-Ph), 69.0 (CH₂—O), 73.4 (≡CH), 78.3 (—C≡), 102.0 (CH3ind), 103.3 (CH4ind), 109.5 (CH7ind), 112.0 (CH6ind), 126.8 (CHPh), 127.4 (C3aind), 128.0 (2×CHPh), 129.2 (2×CHPh), 133.32 (C7aind), 136.9 (C2ind), 138.3 (C1'Ph), 153.26 (C5ind); EM (IE) m/z (%): 91 (77) [PhCH₂]⁺, 352 (22) [M-CH₂Ph]⁺, 374 (100) [M-NCH₃CH₂C≡CH)]⁺, 404 (7) [M-CH₂C≡CH)]⁺, 428 (5) [M-CH₃]⁺, 443 (40)[M]⁺. Anal. Calcd. for C₂₉H₃₇N₃O): C, 78.51; H, 8.41; N, 9.47. Found: C, 78.36; H, 8.31; N, 9.23.

6.2×HCl: pf 203-5° C.; IR (KBr) 3193, 2937, 2512, 1619, 1486, 1469, 1209 cm⁻¹. Anal. Calcd. for C₂₉H₃₉Cl₂N₃O: (516.55): C, 67.43; H, 7.61; N, 8.13; Cl, 13.73. Found: C, 67.38; H, 7.81; N, 8.02; Cl, 13.13.

1.9. Synthesis of dihydrochloride of N-((5-[4-(1-benzylpiperidin-4-yl)butoxy)-1-methyl-1H-indol-2-yl)methyl)-N-methylprop-2-yn-1-amine (7)

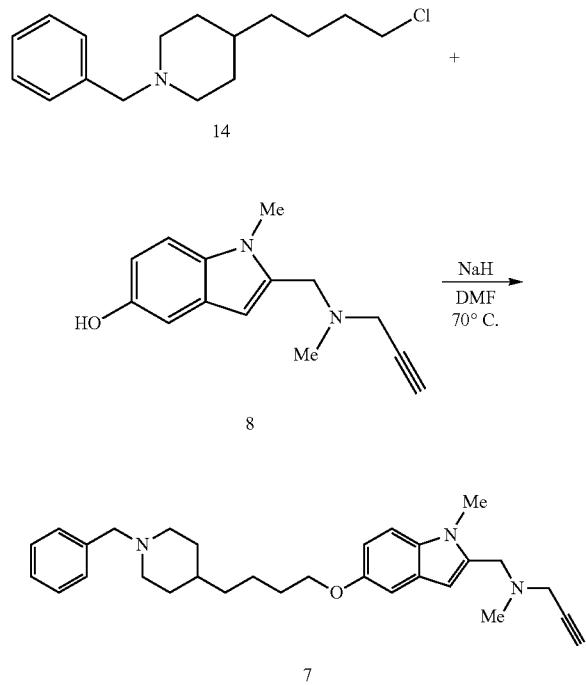

Following the same procedure, but starting from 1-benzyl-4-(4-chloropropyl)piperidine 14 (0.5 g, 1.88 mmol, 1.2 equiv) and 1-methyl-2-{[methyl(prop-2-yn-1-yl)amino]methyl}-1H-indol-5-ol. 8 (Cruces, M. A.; Elorriaga, C.; Fernández-Álvarez, E. *Eur. J. Med. Chem.* 1991, 26, 33-41) (0.358 g, 1.56 mmol) in dry DMF (8 mL), product 7 was obtained (0.547 g, 76%): R_f=0.28 (CH₂Cl₂/MeOH, 20/1); pf 93-4° C.;

IR (KBr) ν 3260, 2937, 2918, 1619, 1489, 1472, 1203, 1193, 1160, 1008 cm⁻¹; RMN of ¹H— (500 MHz, CDCl₃) δ 1.22-134 [m, 4H, CH₂pip+CH₂—(CH₂)₃], 1.45-1.51 (m, 2H, CH₂—(CH₂)₂O), 1.66 (br d, J=9.4 Hz, CH₂pip), 1.73-183 (m, 2H, CH₂—CH₂O) 1.85-2.00 (m, CH₂pip), 2.28 (t, J=2.4 Hz, C≡CH), 2.34 (s, 3H, N—CH₃), 2.88 (d, J=10.5 Hz, CH₂pip), 3.31 (d, J=2.4 Hz, 2H, CH₂—C≡CH), 3.49 (s, 2H, CH₂-Ph), 3.67 (s, 2H, CH₂—N), 3.73 (s, 3H, N—CH₃), 3.98 (t, J=6.6 Hz, 2H, —CH₂—O—), 6.32 (s, 1H, CH-3), 6.85 (dd, J=8.8 and 2.4 Hz, 1H, CH6ind), 7.03 (d, J=2.3 Hz, 1H, CH4ind), 7.17 (d, J=8.8 Hz, 1H, CH7ind), 7.23-7.32 (m, 5H); RMN of ¹³C (125 MHz, CDCl₃) δ 23.3 [CH₂—(CH₂)₂O], 29.7 (CH₂—CH₂O), 29.8 (Nind-CH₃), 32.3 (2×CH₂pip), 35.69 (CH), 36.3 CH₂—(CH₂)₃O], 41.7 (N—CH₃), 44.7 (CH₂—C CH), 51.8 (N—CH₂-ind), 53.9 (2×CH₂pip), 63.5 (CH₂-Ph), 68.8 (CH₂—O), 73.4 (≡CH), 78.4 (—C≡), 102.0 (CH3ind), 103.4 (CH4ind), 109.5 (CH7ind), 112.0 (CH6ind), 126.8 (CHPh), 127.5 (C3aind), 128.1 (2×CHPh), 129.2 (2×CH₂Ph), 133.3 (C7aind), 137.0 (C2ind), 138.5 (C1'Ph), 153.52 (C5ind); EM (IE) m/z (%): 91 (55) [PhCH₂]⁺, 172 (71), 228 (45), 366 (41) [MBz]⁺, 388 [M-NCH₃CH₂C≡CH)]⁺, 418 (8) [M-CH₂C≡CH)]⁺, 457 (26) [M]⁺. Anal. Calcd. for C₃₀H₃₉N₃O: C, 78.73; H, 8.59; N, 9.18. Found: C, 78.65; H, 8.71; N, 9.07.

7.2×HCl: pf 197-9° C.; IR (KBr) ν 3421, 3195, 2928, 2851, 2561, 2509, 1619, 1485, 1472, 1458, 1408, 1209, 1160 cm⁻¹. Anal. Calcd. for (C₃₀H₃₉N₃O.2HCl) (529, 26): C, 67.91; H, 7.79; Cl, 13.36; N, 7.92. Found: C, 67.54; H, 7.45; Cl, 13.25; N, 8.10.

2. Pharmacological Studies

2.1. Studies on the Inhibition of Acetylcholinesterase and Butyrylcholinesterase The inhibitory activity of the enzyme acetylcholinesterase (AChE) was evaluated by the Ellman method (Biochem. *Pharmacol.* 1961, 7, 88) using an electric eel as an AChE neuronal model (*Electrophorus electricus*) and acetylthiocholine iodide (0.35 mM) as substrate. The reaction took place in a final volume of 3 mL of a 0.1 M phosphate buffer solution, pH 8.0, containing 0.035 units of AChE and used a 0.35 mM solution of 5,5'-dithio-bis(2-nitrobenzoic acid) (DTNB) to produce the 5-thio-2-nitrobenzoic acid anion. Inhibition curves were performed in triplicate by incubating at least nine inhibitor concentrations for 10 min. A triplicate sample without inhibitor was always present so as to be aware of 100% of the AChE activity. After this time, the substrate was added to 0.35 mM acetylthiocholine iodide, from a 10 mM stock solution. Loss of color was observed at 412 nm in a spectrophotometric reader having 96 well plates. Determinations of BuChE inhibitory activity, extracted from horse serum, were performed similarly, using 0.05 units/ml BuChE, 0.35 mM 5,5'-dithio-bis-2-nitrobenzoic acid (DTNB) and 0.5 mM butyrylthiocholine iodide from a 10 mM stock solution in a final volume of 3 mL. A triplicate sample without inhibitor was always present so as to be aware of 100% of the BuChE activity. Data from concentration-inhibition experiments of the inhibitors was calculated by non-linear regression analysis using the Origin package which gives estimates of the IC₅₀ (drug concentration producing 50% inhibition of enzyme activity). The results are expressed as Mean±S.E.M. of at least four experiments performed in triplicate. DTNB, acetylthiocholine iodide, butyrylthiocholine iodide.

TABLE 1

Pharmacological data of propargylamine derivatives 1-7, tacrine and donepezil as reference samples. Values are expressed as mean standard error of the mean of at least four experiments. Inhibitory concentration $CI_{50}$ (μM) of the AChE activity (electric eel) or BuChE (horse serum).

| Compound | IC50 (μM) ChE | | |
|---|---|---|---|
|  | EeAChE | eqBuChE | BuChE/AChE |
| 1 | >100 | 0.8 ± 0.1 | — |
| 2 | 18.1 ± 0.4 | 2.2 ± 0.4 | 0.12 |
| 3 | >100 | 7.6 ± 0.4 | — |
| 4 | 0.31 ± 0.04 | 1.1 ± 0.2 | 3.5 |
| 5 | 0.42 ± 0.04 | 2.1 ± 0.2 | 5 |
| 6 | 0.35 ± 0.004 | 0.46 ± 0.065 | 1.3 |
| 7 | 0.26 ± 0.07 | 0.99 ± 0.08 | 3.8 |
| Donepezil | 6.7 ± 0.35 (nM) | 7.4 ± 0.1 | 1104.5 |
| Tacrine | 27 ± 2 (nM) | 5.2 ± 0.2 (nM) | 0.19 |

2.2. Studies on the Inhibition of Monoamine Oxidases (MAO)

The inhibitory activity of monoamine oxidases A and B was assessed by the Fowler and Tipton radiometric method (*Biochem Pharmacol* 1981, 30, 3329) using a purification of rat liver mitochondria as the source of enzymes. The inhibitory activity of MAO-B was compared to 25 μl of [$^{14}$C]-phenylethylamine (PEA), 20 μM of activity, 2.5 mCi/mmol. The inhibitory activity of MAO-A was compared to 25 μl of [$^{14}$C]-(5-hydroxytryptamine) (5-HT), 100 μM of activity, 0.5 mCi/mmol. Inhibition curves were performed in triplicate by incubating at least nine inhibitor concentrations for 30 min. A triplicate sample without inhibitor was always present so as to be aware of 100% of the MAO activity. The reaction took place with the addition of the substrate in a final volume of 225 μl of 50 mM phosphate buffer, pH 7.4, containing 20 μl of rat liver mitochondria at a concentration of 5 mg/ml. The reaction was carried out under continuous stirring at 37° C. for 4 minutes in the case of MAO-B and 20 minutes in the case of MAO-A. The test ended with the addition of 100 μl of 2M citric acid. The aldehydes produced were obtained after adding 4 ml of a solution of toluene:ethyl acetate (1:1, v/v) containing 0.6% (w/v) 2-5-diphenyloxazole (PPO) and the vials were stirred for 1 minute leaving them at −80° C. for 20 min. Thus, freezing was produced in the aqueous phase, where the substrate is not metabolized, and the organic phase was decanted where the aldehyde produced. The radioactivity of the organic phase was read on a Tri-Garb 2810TR scintillation counter, with a counting time of 1 minute per vial. From the disintegration per minute (dpm) data obtained, the specific enzyme activity was calculated (pmol/min·mg protein) with the following equation:

$$\mathrm{dpm} \cdot (100/X) \cdot Y \cdot (1/t \text{ min reaction}) \cdot (1/\mu l \text{ prot}) \cdot (1000/P) = \mathrm{pmol/min \cdot mg\ prot}$$

Where:
X is the extraction ratio of the aldehyde in the organic phase {Fowler, 1980 57/id}, and it is 74.4% for the serotonin aldehyde and 92.5% for the phenylethylamine aldehyde. Y is the dpm to pmol conversion factor, which depends on the activity of the substrate and is 0.9 for serotonin and 0.18 for phenylethylamine. Lastly, P is the concentration of protein used expressed in mg/ml.

The analysis data were calculated by nonlinear regression, sigmoidal dose-response, using GraphPad Prism 3.0 program from which the $IC_{50}$ estimates were obtained for each of the inhibitors. The results were expressed as Mean±SEM of at least three experiments performed in triplicate.

TABLE 1

Pharmacological data of propargylamine derivatives 1-7, tacrine and donepezil as reference samples. Values are expressed as mean standard error of the mean of at least four experiments. Inhibitory concentration $CI_{50}$ (μM) of the activity of monoamine oxidases, MAO-A and MAO-B.

| Compound | IC50 (μM) MAO | | |
|---|---|---|---|
|  | MAO-A | MAO-B | B/A |
| 1 | 143 ± 44.3 | 1457 ± 499 | 10.2 |
| 2 | 65.4 ± 17.4 | 11320 ± 2380 | 173.1 |
| 3 | 30.5 ± 13.5 | 1640 ± 707 | 53.8 |
| 4 | 82.2 ± 3.2 | 745.4 ± 19.9 | 9.1 |
| 5 | 6.7 ± 1.8 | 129.6 ± 41.4 | 19.3 |
| 6 | 5.2 ± 1.1 | 43.1 ± 7.9 | 8.3 |
| 7 | 10.5 ± 4.4 | 2774 ± 116 | 264.2 |
| Donepezil | 854800 ± 13300 | 15400 ± 2200 | 0.02 |
| Tacrine | 40.3 ± 10.6 | 499.6 ± 12.8 | 12.4 |

The invention claimed is:

1. A compound of formula (I)

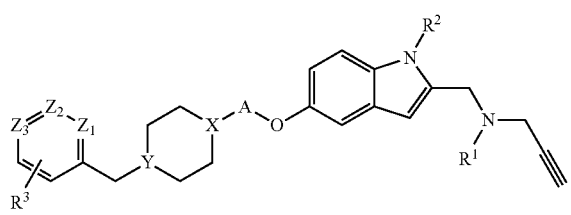

where,
R$^1$ and R$^2$ are selected from H and C$_1$-C$_{10}$ alkyl,
R$^3$ is selected from H, —OR$_4$, N, —CN, —C(O)R$_4$, —C(O)OR$_4$, —C(O)NR$_4$R$_5$, —C═NR$_4$, —OC(O)R$_4$, —NR$_4$R$_5$, —NR$_4$C(O)R$_5$, —NO$_2$, —N═CR$_4$R$_5$, halogen and C$_1$-C$_{10}$ alkyl,
where R$_4$ and R$_5$ are selected from H, alkyl, alkenyl, cycloalkyl and aryl,
X and Y are selected independently from CH and N,
Z$_1$, Z$_2$ and Z$_3$ are CH,
A is selected from (CH$_2$)$_n$, and CO, where n is a whole number from 1 to 6,
or their salts and isomers.

2. The compound according to claim 1 where R$_3$ is H.

3. The compound according to claim 1 where R$^1$ and R$^2$ are independently a C$_1$-C$_4$ alkyl.

4. The compound according to claim 1, which is of formula (II):

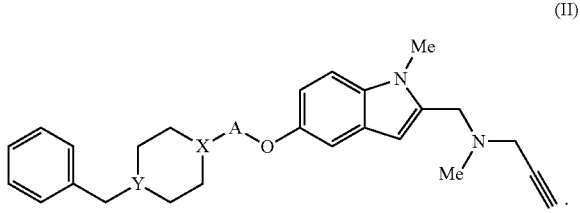

5. The compound according to claim 4, where A is a (CH$_2$)$_n$ group, where n is a whole number from 1 to 4.

6. The compound according to claim 4 where X is N.

7. The compound according to claim 4 where Y is N.

8. The compound according to claim 1, selected from the group consisting of:

N-((5-(2-(4-benzylpiperidin-1-yl)ethoxy)-1-methyl-1H-indol-2-yl)methyl)-N-methylprop-2-yn-1-amine, N-((5-(3-(4-benzylpiperidin-1-yl)propoxy)-1-methyl-1H-indol-2-yl)methyl)-N-methylprop-2-yn-1-amine, N-((5-(3-(4-benzylpiperazine-1-yl)propoxy)-1-methyl-1H-indol-2-yl)methyl)-N-methylprop-2-yn-1-amine, N-((5-((1-benzylpiperidin-4-yl)methoxy)-1-methyl-1H-indol-2-yemethyl)-N-methylprop-2-yn-1-amine, N-((5-(2-(1-benzylpiperidin-4-yl)ethoxy)-1-methyl-1H-indol-2-yl)methyl)-N-methylprop-2-yn-1-amine, N-((5-(3-(1-benzylpiperidin-4-yl)propoxy)-1-methyl-1H-indol-2-yl)methyl)-N-methylprop-2-yn-1-amine, and N-((5-(4-(1-benzylpiperidin-4-yl)butoxy)-1-methyl-1H-indol-2-yl)methyl)-N-methylprop-2-yn-1-amine.

9. The compound according to claim 1, selected from the group consisting of:

Dihydrochloride of N-((5-(2-(4-benzylpiperidin-1-yl)ethoxy)-1-methyl-1H-indol-2-yl)methyl)-N-methylprop-2-yn-1-amine, Dihydrochloride of N-((5-(3-(4-benzylpiperidin-1-yl)propoxy)-1-methyl-1H-indol-2-yl)methyl)-N-methylprop-2-yn-1-amine, Trihydrochloride of N-((5-(3-(4-benzylpiperidin-1-yl)propoxy)-1-methyl-1H-indol-2-yl)methyl)-N-methylprop-2-yn-1-amine, Dihydrochloride of N-((5-((1-benzylpiperidin-4-yl)methoxy)-1-methyl-1H-indol-2-yl)methyl)-N-methylprop-2-yn-1-amine, Dihydrochloride of N-((5-(2-(1-benzylpiperidin-4-yl)ethoxy)-1-methyl-1H-indol-2-yl)methyl)-N-methylprop-2-yn-1-amine, Dihydrochloride of N-((5-(3-(1-benzylpiperidin-4-yl)propoxy)-1-methyl-1H-indol-2-yl)methyl)-N-methylprop-2-yn-1-amine, and Dihydrochloride of N-((5-(4-(1-benzylpiperidin-4-yl)butoxy)-1-methyl-1H-indol-2-yl)methyl)-N-methylprop-2-yn-1-amine.

10. The compound according to claim 1, characterized in that it is an isomer of one of the compounds selected from the group consisting of:

Dihydrochloride of N-((5-(2-(4-benzylpiperidin-1-yl)ethoxy)-1-methyl-1H-indol-2-yl)methyl)-N-methylprop-2-yn-1-amine, Dihydrochloride of N-((5-(3-(4-benzylpiperidin-1-yl)propoxy)-1-methyl-1H-indol-2-yl)methyl)-N-methylprop-2-yn-1-amine, Trihydrochloride of N-((5-(3-(4-benzylpiperidin-1-yl)propoxy)-1-methyl-1H-indol-2-yl)methyl)-N-methylprop-2-yn-1-amine, Dihydrochloride of N-((5-((1-benzylpiperidin-4-yl)methoxy)-1-methyl-1H-indol-2-yl)methyl)-N-methylprop-2-yn-1-amine, Dihydrochloride of N-((5-(2-(1-benzylpiperidin-4-yl)ethoxy)-1-methyl-1H-indol-2-yl)methyl)-N-methylprop-2-yn-1-amine, Dihydro chloride of N-((5-(3-(1-benzylpiperidin-4-yl)propoxy)-1-methyl-1H-indol-2-yl)methyl)-N-methylprop-2-yn-1-amine, and Dihydrochloride of N-((5-(4-(1-benzylpiperidin-4-yl)butoxy)-1-methyl-1H-indol-2-yl)methyl)-N-methylprop-2-yn-1-amine.

11. A pharmaceutical composition comprising at least one compound of the formula (I) defined in claim 1 and a pharmaceutically acceptable excipient.

12. The composition according to claim 11 which further comprises another active ingredient.

13. A method to obtain a compound of formula (I) defined in claim 1, comprising the reaction of a compound of formula (V):

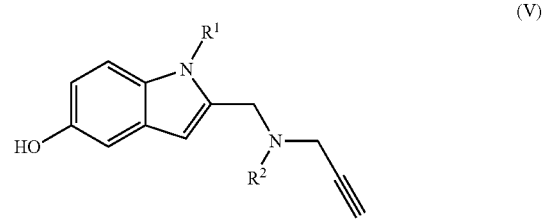

(V)

where $R^1$, $R^2$ are as defined as in claim 1, and a compound of formula (VI):

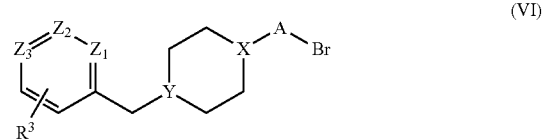

(VI)

where $R^3$, A, X, Y, $Z_1$, $Z_2$ and $Z_3$ are as defined above.

* * * * *